United States Patent
Pijoan

(10) Patent No.: US 6,585,981 B1
(45) Date of Patent: Jul. 1, 2003

(54) TEMPERATURE-SENSITIVE LIVE VACCINE FOR MYCOPLASMA HYOPNEUMONIAE

(75) Inventor: Carlos Pijoan, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/627,006

(22) Filed: Jul. 27, 2000

(51) Int. Cl.[7] ................................................ A61K 39/02
(52) U.S. Cl. .................. 424/264.1; 424/234.1; 424/253.1; 424/255.1; 424/256.1; 424/204.1; 424/197.11; 424/196.11; 424/201.1; 424/203.1; 424/274.1
(58) Field of Search ......................... 424/234.1, 264.1, 424/253.1, 255.1, 256.1, 204.1, 197.11, 196.11, 201.1, 203.1, 274.1

(56) References Cited

U.S. PATENT DOCUMENTS

| | | | |
|---|---|---|---|
| 4,894,332 A | | 1/1990 | Schaller et al. ............ 435/69.3 |
| 5,338,543 A | * | 8/1994 | Fitzgerald et al. |
| 5,788,962 A | | 8/1998 | Wise et al. ............... 424/264.1 |
| 5,968,525 A | * | 10/1999 | Fitzgerald et al. |

FOREIGN PATENT DOCUMENTS

| | | | | |
|---|---|---|---|---|
| EP | 0571648 | | 12/1993 | .......... A61K/39/02 |
| WO | 93/16726 | * | 9/1993 | |

OTHER PUBLICATIONS

Sheldrake et al. Res. in Vet. Sci. 1993. 55: 371–6.*
Okada et al. J. Vet. Med. Sci., Oct. 1999, 61(10): 1131–5.*
Wang et al. Scientia Agricultura Sincia, 1990, 23(1): 1–8, Abstract Only.*
Li et al. Scientia Agricultura Sincia, 1989, 22(4): 1–8, Abstract Only.*
Cruse et al. Illustrated Dictionary of Immunology. 1995. p. 35.*
Lam, et al, "Temperature–sensitive mutants of mycoplasma . . . " J. Comp. Path 94:1–8. 1984.*
Lai, et al, "Biological evaluation of mycoplasma pulmonis temperature–sensitive mutants . . . " Infect. and Imm. 58(7):2289–96 1990.*
Friis, N..F., "Some Recommendations Concerning Primary Isolation of Mycoplasma suipneumoniae and Mycoplasma flocculare—A Survey", Norkisk Veterinaermedicin, 27, (1975), pp. 337–339.

Calsamiglia, M., et al., "Application of a nested polymerase chain reaction assay to detect Mycoplasma hyponeumoniae from nasal swabs", J. Vet Diagn Invest, 11, pp. 246–251, (1999).
Dybvig, K., et al., "Construction of recA Mutants of Acholeplasma laidlawii by Insertional Inactivation with a Homologous DNA Fragment", Plasmid, 28, pp. 262–266, (1992).
Dybvig, K., et al., "Transformation of Mycoplasma pulmonis and Mycoplasma hyorhinis: Transposition of Tn916 and Formation of Cointegrate Structures", Plasmid, 20, pp. 33–41, (1988).
Friis, N.F., "Some Recommendations Concerning Primary Isolation of Mycoplasma suipneumoniae and Mycoplasma flocculare—A Survey", Norkisk Veterinaermedicin, 27, pp. 337–339, (1975).
Goodwin, R.F., et al., "Enzootic Pneumonia of Pigs: Immunization Attempts Inoculating Mycoplasma Suipneumoniae Antigen by Various Routes and with Different Adjuvants", Br. Vet. J., 129, pp. 456–462, (1973).
Hedreyda, C.T., et al., "Transformation of Mycoplasma pneumoniae with Tn4001 by Electroporation", Plasmid, 30, pp. 170–175, (1993).
Lai, W.C., et al., "Biological Evaluation of Mycoplasma pulmonis Temperature–Sensitive Mutants for Use as Possible Rodent Vaccines", Infection and Immunity, 58 (7), pp. 2289–2296, (Jul. 1990).
Lam, K.M., et al., "Temperature–Sensitive Mutants of Mycoplasma Gallisepticum", J. Comp. Path. 94, pp. 1–8, (1984).
McGhee, J., et al., "New Perspectives in Mucosal Immunity with Emphasis on Vaccine Development", Seminars in Hematology, 30 (4) Suppl. 4, pp. 3–15, (Oct. 1993).
Meynell, G.G., et al., Theory and Practice In Experimental Bacteriology, Cambridge at the University Press, pp. 12–29, (1965).
Murphy, D.A., et al., "Aerosol vaccination of pigs against Mycoplasma hyponeumoniae infection", Am J Vet Res, 54 (11), pp. 1874–1880, (Nov. 1993).
Solano, G., et al., "A simple technique for tracheal culture to detect respiratory pathogens in live pigs", Swine Health and Production, 5 (1), pp. 30–31, (Jan./Feb. 1997).

* cited by examiner

Primary Examiner—Jennifer E. Graser
(74) Attorney, Agent, or Firm—Schwegman, Lundberg, Woessner & Kluth, P.A.

(57) ABSTRACT

The present invention provides a live temperature-sensitive vaccine for Mycoplasma hyopneumoniae. The present invention also provides methods of vaccinating a swine against colonization or infection of Mycoplasma hyopneumoniae.

17 Claims, No Drawings

TEMPERATURE-SENSITIVE LIVE VACCINE FOR *MYCOPLASMA HYOPNEUMONIAE*

BACKGROUND OF THE INVENTION

Porcine respiratory disease complex (PRDC) is an increasingly important cause of lowered swine productivity as characterized by slow growth, decreased feed efficiency, anorexia, fever, cough, and dyspnea. *Mycoplasma hyopneumoniae*, also called *Mycoplasma suipneumoniae*, is the causative agent of swine mycoplasmal pneumonia (also known as enzootic pneumonia, virus pneumonia, infectious pneumonia, and anterior lobe pneumonia of pigs). *M. hyopneumoniae* is a small, prokaroytic microbe smaller and simpler in structure than bacteria, but more complex than viruses. Unlike viruses, they are capable of a free living existence, through they are often found in association with eukaroytic cells as they have absolute requirements for exogenous sterols and fatty acids which generally necessitates growth in serum-containing media. *M. hyopneumoniae* is bound by a cell membrane but not by a cell wall. They have an extremely small genome, approximately 750,000 base pairs in length. The pig is the only known host of this mycoplasma.

Mycoplasmal pneumonia is one of the most prevalent swine respiratory tract diseases among the pig-raising countries of the world. Surveillance data from PigMon, a monitoring program that evaluates lesions in farms throughout the upper Midwest of the United States, identified pneumonia in 97% of the Midwestern swine herds, with >70% prevalence among the sampled animals (Dybvig 1992). Mycoplasmal pneumonia has a low mortality rate but a high morbidity rate (30–80%). The disease generally results in considerable economic loss, because it causes a depression in growth rate, inefficiency and sickness in animals.

The disease is transmitted from pig to pig through the nasal passages by airborne organisms expelled from infected pigs. The mycoplasma establish themselves deep in the apical and cardiac lobes of the lungs where they cause visible plum colored or gray lesions and cause difficulty in breathing and reduced weight gain. The primary infection by *M. hyopneumoniae* may be followed by secondary infection by other mycoplasma species (e.g., *M. hyorhinus* and *M. floculare*) as well as bacterial pathogens (Pasteurella and Bordetella species). These respiratory tract diseases caused by *M. hyopneumoniae* cause decreased weight gain at a time when animals are being fed for market. Thus, animals which have been infected with this organism will be worth less at slaughter than their non-infected counterparts.

Even though many farms have adopted multiple-site, high health programs, the prevalence of pneumonia has not declined markedly but may be changing in epidemiology. Due to the serious economic consequences of pig pneumonia, vaccines against, and treatments for *Mycoplasma hyopneumoniae* have been sought. Mycoplasma prevention in pigs is accomplished by a mixture of antibiotic treatment and vaccination. This approach has the drawback of being both expensive and unpredictable, with many farms showing little improvement following these procedures. Vaccination against *Mycoplasma hyopneumoniae* is a relatively recent introduction, with vaccines being available commercially only for the last 6–7 years.

Although Mycoplasma vaccines for pigs have been a huge commercial success, their merits under field conditions are still very much under debate. In general, these vaccines reduce average lesion scores of pneumonic lungs at slaughter, but do not impact the prevalence of affected pigs. That is, the same number of pigs are affected, but terminal lesions appear to be smaller. The impact of Mycoplasma vaccination on performance is even more suspect, with few, if any, papers showing a definite improvement in either gain or conversion.

The reason for the relatively unsatisfactory performance of these vaccines may be related to the fact that they are killed bacterins, together with the peculiarities of Mycoplasma infection in pigs. *M. hyopneumoniae* is a non-invading colonizer of ciliated epithelial cells. Because the organism does not invade the respiratory system, circulating antibodies elicited by the killed bacterins must cross the epithelial barrier and be secreted into the tracheobronchial lumen, a process that is difficult and ineffective. Mycoplasma bacterins must be able to elicit high levels of systemic antibodies, in order to be able to achieve this mucosal secretion. This, of course, requires relatively high doses of antigen and aggressive adjuvants, which makes these vaccines expensive and difficult to administer.

Another problem deals with the need to administer currently available vaccines by a double-dose injectable method. Such a double-dose method requires considerable pig handling, which is time-intensive and results in stress to the animals. As farms grow larger, double-dose, injection vaccination methods are becoming increasingly undesirable, with producers requiring an alternative vaccination method that does not require such handling.

Therefore, an ongoing need exists for a safe, effective vaccine against *M. hyopneumoniae* that is easy to administer.

SUMMARY OF THE INVENTION

The present invention provides an isolated and purified temperature-sensitive *Mycoplasma hyopneumoniae* bacterin. The bacterin may be ATCC deposit no. PTA-3549 (deposited in the American Type Culture Collection, 10801 University Blvd., Manassas, Va. 20110-2209, on Jul. 24, 2001).

The present invention also provides a vaccine preparation containing a live temperature-sensitive *Mycoplasma hyopneumoniae* bacterin in combination with a physiologically-acceptable, non-toxic vehicle. The bacterin may be ATCC deposit no. PTA-3549. The vaccine preparation may further contain an immunological adjuvant. Also, the vaccine preparation may contain at least one additional infectious agent. An infectious agent may be a virus, a bacterium, a fungus or a parasite. In particular, the infectious agent may be *Borderella bronchiseptica, Pasteurella multocida* types A or D, or *Haemophilus parasuis*.

The present invention also provides a method of inducing an immune response and/or protecting a susceptible swine against colonization or infection of a *Mycoplasma hyopneumoniae* by administering to the swine an effective amount of a vaccine preparation containing a live temperature-sensitive *Mycoplasma hyopneumoniae* bacterin in combination with a physiologically-acceptable, non-toxic vehicle. The vaccine preparation may further contain an immunological adjuvant. The vaccine may be administered by subcutaneous or intramuscular injection, oral ingestion, or intranasally. The vaccine preparation may be administered in one or more doses.

DETAILED DESCRIPTION OF THE INVENTION

The term "vaccine" is defined herein in its broad sense to mean a biological agent used to produce active immunity.

Vaccines generally employ one of four categories of antigens: live microorganisms administered via an unnatural route, live attenuated microorganisms, killed microorganisms and fractions or even a single antigen or product of a microorganism. In all situations, the goal is to present antigens without giving the disease. A number of different inactivating agents and means have been employed including formalin, azide, freeze-thaw, sonication, heat treatment, sudden pressure drop, detergent (especially non-ionic detergents), lysozyme, phenol, proteolytic enzymes and propiolactone. Examples of vaccines include those described in U.S. Pat. Nos. 4,894,332; 5,788,962; 5,338,543; and 5,968,525; and EP 571,648.

An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response.

Moreover, the goal of a vaccine is to provide protection against natural infection. A detectable immune response, such as producing detectable quantities of antibodies, may not necessarily be protective. Thus, while previous vaccines have been attempted to protect swine from infection by *Mycoplasma hyopneumoniae*, acceptable levels of protection have not been achieved.

An alternative to presently-available Mycoplasma vaccines for use in pigs is to use a live vaccine. Such a live vaccine would have many advantages. For example, local immunization could be achieved by delivering the vaccine directly to mucosal sites in an aerosol preparation, only one dose of vaccine would be needed, it would be cheaper to manufacture. The present inventors prepared temperature-sensitive mutants that fail to grow at normal pig temperatures but can grow in vitro at cooler temperatures.

Briefly, *M. hyopneumoniae* was mutated by being exposed to N-methyl-N-nitro-N-nitrosoguanidine. The mutated *M. hyopneumoniae* was grown in Friis media, treated with nitrosoguanidine, and then grown on a Friis agarose plate for 10 to 14 days. Each plate containing well-separated colonies was replicated onto a nitrocellulose filter and used for epifluorescence to detect the presence of cytoplasmic LDH. Colonies not expressing LDH were selected and used for the animal studies. Organisms exposed to nitrosoguanidine were grown at 34° C. Colonies were blotted onto nitrocellulose and transferred to agar plates and incubated at 39° C. Colonies growing at 34° C. but not at 39° C. were selected and deposited with ATCC (ATCC deposit no. PTA-3549.).

For the preparation of a vaccine protective against infection from *M. hyopneumoniae*, the present invention employs live, temperature-sensitive bacteria. Many microorganisms lose their infectivity and change antigens when grown in culture for many generations. Indeed, the standard vaccine for polio is essentially a live polio virus which after growing in culture for many generations has mutated so that it no longer grows in nerve or brain tissue and thus has lost much of much of its pathogenicity. For this virus, the critical antigens have not changed.

Suitable strains of *M. hyopneumoniae* may be obtained from a variety of sources. Strains may be obtained from depositories such as the ATCC and NRRL. In view of the widespread dissemination of the disease, numerous strains may easily be obtained by recovering *M. hyopneumoniae* from lung secretions or tissue from sick animals and inoculating suitable culture medium.

The present live, temperature-sensitive *M. hyopneumoniae*, also called a *M. hyopneumoniae* "bacterin," is employed directly as a vaccine. The effective amount will depend on the species, breed, age, size, health status and whether the animal has previously been given a vaccine against the same organism. The additional components in the vaccine and route of administration will also affect the effective dosage. Each batch of bacterin may be individually calibrated. The effective dosage is easily determinable by one of ordinary skill in the art by methodical trials of different dosages.

The term "protecting" or "protection" when used with respect to the vaccine for mycoplasmal pneumonia caused by *M. hyopneumoniae* described herein means that the vaccine prevents the incidence of mycoplasmal pneumonia caused by *M. hyopneumoniae*, prevents the colonization of *M. hyopneumoniae*, or ameliorates or reduces the severity of the disease in the swine.

The dosage of vaccine to administer is easily determinable based on the concentration of bacterin, the route of administration and the condition of the animal. The effective amount is readily determined by one skilled in the art. The critical factor is that the dosage provides at least a partial protective effect against natural infection. Thus, an effective dose of vaccine is an amount of vaccine sufficient to afford protection in swine against mycoplasmal pneumonia. This dose will elicit an immunological response in a host animal.

In a preferred embodiment of this invention, an effective dose of vaccine is determined to be about $10^6$ to $10^9$ colony forming units (CFU)/ml, and preferably about $10^6$ to $10^7$ CFU/ml. The active ingredient may typically range from about 1% to about 95% (w/w) of the composition, or even higher or lower if appropriate. The quantity to be administered depends upon factors such as the age, weight and physical condition of the animal considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the vaccine in one or more doses. Multiple doses may be administered as is required to maintain a state of immunity to the organism.

The vaccine preparation may include one or more adjuvants to heighten the immune response sufficiently to substantially prevent natural infection. Adjuvant refers to any substance whose admixture with an injected immunogen increases the response. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. (McGhee 1993).

A widely used procedure involves the administration of inorganic gels, for example, alum, aluminum hydroxide, or aluminum phosphate. Some of the most effective adjuvants are water-in-oil emulsions, particularly those in which living or dead mycobacteria are suspended, e.g. complete Freund's adjuvant. However, emulsions without mycobacteria (incomplete Freund's adjuvant) are less irritating and are often used. To enhance immunogenicity of a bacterin, adjuvants containing aluminum hydroxide and/or DEAE dextran (diethyl amino ethylether dextran) may be used. The concentration of aluminum hydroxide may be very broad, in the range of up to about 1.5% depending on the route of administration. Concentrations in the range of 0.1 to 1.0% are more typical. Likewise the concentration of DEAE dextran may be wide, e.g., up to about 6% may be used. Concentrations of aluminum hydroxide and DEAE dextran in the vaccine may be from about 0.24% to about 0.39% aluminum hydroxide and about 1.5% of DEAE dextran.

DEAE dextran is commercially available in a variety of molecular weights. While the examples use DEAE dextran with a molecular weight of 500,000 daltons, different sizes may also be used as an adjuvant. Dextran sulfate has been used as an adjuvant but the results were less impressive.

The optimum concentrations of aluminum hydroxide and DEAE dextran would be readily determined by those using this invention by varying concentrations of each in the presence of fixed concentrations of the other and determining which is most protective.

The bacterin, whether it is with an adjuvant or not, may be admixed with a acceptable vehicle for vaccination. Well known examples include sterile water, saline, or buffered solutions. Additional agents to improve suspendability and dispersion in solution may also be used. Many conventional vehicles for carrying a vaccine are known and are mentioned in the references above. It is within the abilities of those skilled in the art to select appropriate vehicles depending on the route of administration and condition of the recipient animal.

Immunization may be performed by any of the methods well known to those skilled in the art such as oral, intranasal, aerosol and injection (either IM, SC, IV, ID or other method). The route of administration depends on the animal being vaccinated, vaccination history and convenience of the person administering the vaccine. The preferred route of administration is intranasally. For example, the vaccine may be administered via aerosol vaccination (Murphy 1993). This route of administration is preferred because the nature of protective immunity for *M. hyopneumoniae* may be local (pulmonary) immunity and cell-mediated immunity in preventing the disease rather than from circulating antibodies. Presentation of antigen (vaccine) to the respiratory tract immune system may stimulate a local immune response. Therefore localized administration of the vaccine may be more effective. Further, by administering the vaccine as an aerosol in an enclosed barn or space and allowing the pigs to inhale it, reduces the labor involved in vaccinating large numbers of animals in intensive production systems. Aerosol vaccination also, referred to as spray vaccination, is currently used on a commercial basis to effectively vaccinate poultry against certain diseases.

Repeated vaccinations may be administered at periodic time intervals to enhance the immune response initially or after a long period of time since the last dose. The time interval between vaccinations varies depending on the age and condition of the animal. For initial vaccination, the period will generally be longer than a week and preferably will be between about two to three weeks. For previously vaccinated animals, approximately annual, before or during pregnancy inoculations may be performed.

*M. hyopneumoniae* bacterin may be used alone or in combination with other vaccines for convenience or enhanced results. The combination vaccine preferably provides protection against plural infections. Of particular interest is the combination of *M. hyopneumoniae* and *Borderella bronchiseptica* and *Pasteurella multocida* types A and D because all three cause significant disease in swine. Additionally, such combinations do not interfere with each other in their ability to stimulate a protective immune response. These other vaccines may be inactivated by entirely different means. The other vaccines to be combined with *M. hyopneumoniae* bacterin should also be compatible with the same adjuvant used for *M. hyopneumoniae* bacterin.

Lung score or lung lesion score refers to the extent of lesions detectable in lung tissue. The scoring system is carried out as described by Goodwin and Whittlestone (1973) *Br. Vet. J.* 129:456–462.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the live, temperature-sensitive *M. hyopneumoniae* are isolated. The amount of *M. hyopneumoniae* may then be adjusted to an appropriate concentration, optionally combined with a suitable vaccine adjuvant, and packaged for use.

The following examples are intended to illustrate but not limit the invention.

EXAMPLES

Example 1

Preparation of Temperature-sensitive Mutants of *Mycoplasma hyopneumoniae*

*M. hyopneumoniae* was mutated following exposure to N-methyl-N-nitro-N-nitrosoguanidine. This method has been successfully used in several mycoplasmas (Lam 1984, Lai 1990). *M. hyopneumoniae* was grown in Friis media, treated with 100 mg/ml nitrosoguanidine, and then grown on a Friis agarose plate for 10 to 14 days. Organisms exposed to nitrosoguanidine were grown at 34° C. Colonies were then blotted onto nitrocellulose and transferred to agar plates and incubated at 39° C. Colonies that grew at 34° C. but not at 39° C. were selected for further use. Selected mutants were then cloned three times and kept at −80° C. until further use. Isolates were deposited with ATCC (ATCC deposit no. PTA-3549.).

Example 2

Vaccine Preparation

To prepare the vaccine, one of the selected mutants (ATCC deposit no. PTA-3549.) was grown at 34° C. on Friis media until turbidity and an acid color change were evident. Colony-forming units (cfu) were determined by tenfold dilutions in Friis broth, using five replicates per dilution. Vaccine was used as a fresh broth culture, without adjuvant addition.

Example 3

Pig Vaccination Pilot Study

A small pilot project was done in order to preliminarily evaluate the safety and effectiveness of the vaccine. To do this, 16, five-day-old piglets from a Mycoplasma-free farm were obtained and housed in the isolation units of the College of Veterinary Medicine, University of Minnesota.
Experimental Protocol Animals were randomly assigned to two groups of eight pigs each and received the following treatments:

| Group | Animals | Vaccination | Challenge | Necropsy |
|---|---|---|---|---|
| 1 | 4 | intranasal (2 doses) | 12 days postvac. | 7 weeks |
| 1 | 4 | intramascular (1 dose) | same | 7 weeks |
| 2 | 4 | placebo (2 doses) | same | same |
| 2 | 4 | intramuscular | none | days 1, 2, 3, 7 |

This design was made so that both a mucosal presentation of the vaccine (intranasal) and a parenteral presentation (intramuscular) were tested. Group two included non-vaccinated, challenged controls, as well as vaccinated unchallenged animals that were used to evaluate product safety.
Parameters Monitored Pigs were monitored weekly for body temperature and for respiratory signs suggestive of Mycoplasma infection. They were also tested weekly for the presence of *M. hyopneumoniae* in their nasal cavities using a PCR technique (Calsamiglia 1999). At necropsy, all animals were evaluated for macroscopic and microscopic pulmonary lesions. Presence of *M. hyopneumoniae* was assessed by PCR and bacterial culture from tracheobronchial swabs. Animals were also evaluated at this time for the presence of Mycoplasma antibodies using a standard ELISA technique.
Results
Mutant Production and Selection Temperature-sensitive mutants that grew at 34, but not at 39° C., were successfully produced. Two mutant colonies were selected, cloned and frozen. One of the mutant colonies (MNtemp-1) was then passaged three times and tested for stability. The mutant strain did not revert and was unable to grow at 39° C. following this treatment. Identity of the mutant as *M. hyopneumoniae* was established by PCR.
Pilot Study
Vaccine Safety All vaccinated pigs, regardless of route, maintained a normal temperature of 38.5 to 39.5° C. Also, these animals presented no clinical evidence of respiratory distress during the observation period. Pigs vaccinated, but not challenged, had no obvious macroscopic or microscopic lesions at the injection site at the observed dates (1, 2, 3 and 7 days post-vaccination).
Vaccine Potency Vaccination dose was $10^8$ cfu/ml.
Vaccine Efficacy None of the intramuscular-vaccinated piglets presented macroscopic pneumonic lesions at slaughter. One of these animals (¼) had a small microscopic lesion with mild peribronchial mononuclear infiltrate. This animal yielded *M. hyopneumoniae* on culture from tracheobronchial washings and swabs. Similarly, one of the intranasal vaccinates showed a small macroscopic pneumonic lesion (3% lung affected), with peribronchial mononuclear infiltrate and some pericardial fluid accumulation. This animal also yielded *M. hyopneumoniae* on culture at necropsy and was positive to the fluorescent antibody assay. The rest of the vaccinated challenged pigs (⅞) had no macroscopic or microscopic lesions and yielded no positive *M. hyopneumoniae* from tracheobronchial samples.

In contrast, three unvaccinated challenged animals (¾) had macroscopic (9, 9 and 20% of lung affected) and all had microscopic lesions of pneumonia. All animals were fluorescence positive and yielded *M. hyopneumoniae* on tracheobronchial culture. These pigs had a temperature of >39.5° C. the 4 days following challenge. Additionally, ¾ animals had clinical signs of cough and dyspnea. None of the pigs, regardless of treatment, seroconverted to Mycoplasma as assessed by the Tween-ELISA technique used.
Discussion A temperature-sensitive mutant (MNtemp-1) was successfully produced through random mutation following exposure to nitrosoguanidine. After cloning, the MNtemp-1 strain proved stable for at least three passages and did not revert to the wild type. Purity of the strain was confirmed by standard PCR identification.

In the pilot study, a live vaccine prepared with MNtemp-1 proved successful in completely protecting ⅞ pigs following challenge with a virulent *M. hyopneumoniae*. One animal in each group had small microscopic lesions and yielded a positive culture of *M. hyopneumoniae* at necropsy. One of these animals also had a small (3%) macroscopic lesion. Conversely, the unvaccinated pigs had larger lesion scores, 75% of them presented with macroscopic lesions, 100% with microscopic lesions and they were all positive to the fluorescent antibody assay. Also, all of these control animals yielded positive Mycoplasma cultures from tracheobronchial washings.

These results show that a stable temperature-sensitive mutant of *Mycoplasma hyopneumoniae* was successfully produced. They also suggest that this mutant can be successfully used as a vaccine against swine pneumonia caused by this agent.

All publications and patents are herein incorporated by reference to the same extent as if each individual publication or patent application was specifically and individually indicated to be incorporated by reference. It will be apparent to one of ordinary skill in the art that many changes and modifications can be made in the invention without departing from the scope of the appended claims.
References Calsamiglia, M., Pijoan, C. and Trigo A. (1999): Application of a nested polymerase chain reaction assay to detect *Mycoplasma hyopneumoniae* from nasal swabs. *J. Vet. Diag. Invest.* 11:246–251.

Dybvig, K., A. Woodard, Construction of recA mutants of *Acholeplasma laidlawii* by insertional inactivation with a homologous DNA fragment, *Plasmid*, 28, 262–266 (1992).

Dybvig, K., G. H. Cassell, Transposition of gram-positive bacterial transposon Tn916 in *Acholeplasma laidlawii* and *Mycoplasma hyorhinis*: transposition of Tn916 and formation of cointegrate structures, *Plasmid*, 20, 33–41 (1988).

Friis, N F, Mycoplasms of the swine: A Review, Norkisk Veterinaermedicin, 27, 329–36 (1975).

Friis, N F, Some recommendations concerning primary isolation of *Mycoplasma suipneumoniae* and *Mycoplasma flocculare*: A Survey, Norkisk Veterinaermedicin, 27, 337–9 (1975).

Hedreyda, C. T., K. K. Lee, D. C. Krause, Transformation of *Mycoplasma pneumoniae* with Tn4001 by electroporation, *Plasmid*, 30, 170–175 (1993).

Lai, W. C., M. Benuet, Y. S. Lu, S. P. Pakes, Biological evaluation of *Mycoplasmis pulmonis* temperature sensitive mutants for use as possible rodent vaccines, *Infection and Immunity*, 58(7), 2289–2269 (1990).

Lam, K. M., J. Rosen, Temperature sensitive mutants of *Mycoplasma gallisepticum, J. Comp. Pathol*., 94(1), 1–8 (1984).

McGhee, J. R., et al., On vaccine development, *Sem. Hematol*., 30:3–15 (1993).

Meynell, G. G. and E. Meynell, Theory and practice of experimental bacteriology, Cambridge University Press (1965).

Murphy, D A, et al., Aerosol Vaccination of pigs against *Mycoplasma hyopneumoniae* infection, *Am J. Vet. Res*. 54:1874–80 (1993).

Solano, G. I., C. Pijoan, A simple technique for tracheal culture to detect respiratory pathogens in live pigs, *Swine Hlth. Prod*., 5, 30–31 (1997).

What is claimed is:

1. A live isolated and purified temperature-sensitive *Mycoplasma hyopneumoniae*, wherein the *Mycoplasma hyopneumoniae* was mutated using a chemical agent, and wherein the *Mycoplasma hyopneumoniae* grows at 34° C. but does not grow at 38.5–39.5° C.

2. The *Mycoplasma hyopneumoniae* of claim 1, which is ATCC deposit no. PTA-3549.

3. A vaccine preparation comprising a live temperature-sensitive *Mycoplasma hyopneumoniae*, wherein the *Mycoplasma hyopneumoniae* was mutated using a chemical agent, and wherein the *Mycoplasma hyopneumoniae* grows at 34° C. but does not grow at 38.5–39.5° C., in combination with a physiologically-acceptable, non-toxic vehicle.

4. The vaccine preparation of claim 3, wherein the *Mycoplasma hyopneumoniae* is ATCC deposit no. PTA-3549.

5. The vaccine preparation of claim 3, wherein the vaccine further comprises an immunological adjuvant.

6. The vaccine preparation of claim 5, further comprising at least one additional infectious agent, wherein the infectious agent is a virus, a bacterium, a fungus or a parasite.

7. The vaccine preparation of claim 6, wherein the infectious agent is *Borderella bronchiseptica, Pasteurella multocida* types A or D, or *Haemophilus parasuis*.

8. A method of protecting a susceptible swine against colonization or infection of a *Mycoplasma hyopneumoniae* comprising administering to the swine an effective amount of a vaccine preparation comprising a live temperature-sensitive *Mycoplasma hyopneumoniae*, wherein the *Mycoplasma hyopneumoniae* was mutated using a chemical agent, and wherein the *Mycoplasma hyopneumoniae grows at* 34° C. but does not grow at 38.5–39.5° C., in combination with a physiologically-acceptable, non-toxic vehicle.

9. The method of claim 8 wherein the vaccine preparation further comprises an immunological adjuvant.

10. The method of claim 8 wherein the vaccine preparation is administered by subcutaneous or intramuscular injection, oral ingestion, or intranasally.

11. The method of claim 8 wherein the vaccine preparation is administered intranasally.

12. The method of claim 8 wherein the vaccine preparation is administered in one or more doses.

13. A method for inducing an immune response in a susceptible swine against mycoplasmal pneumonia caused by a *Mycoplasma hyopneumoniae* comprising administering to the swine an effective amount of a vaccine preparation comprising a live temperature-sensitive *Mycoplasma hyopneumoniae*, wherein the *Mycoplasma hyopneumoniae* was mutated using a chemical agent, and wherein the *Mycoplasma hyopneumoniae* grows at 34° C. but does not grow at 38.5–39.5° C., in combination with a physiologically-acceptable, non-toxic vehicle.

14. The method of claim 13 wherein the vaccine preparation further comprises an immunological adjuvant.

15. The method of claim 13 wherein the vaccine preparation is administered by subcutaneous or intramuscular injection, oral ingestion, or intranasally.

16. The method of claim 13 wherein the vaccine preparation is administered intranasally.

17. The method of claim 13 wherein the vaccine preparation is administered in one or more doses.

* * * * *